United States Patent [19]

McGhee et al.

[11] Patent Number: 5,451,697

[45] Date of Patent: Sep. 19, 1995

[54] PROCESS FOR PREPARING ISOCYANATES

[75] Inventors: William D. McGhee, Bridgeton; Mark D. Paster, Chesterfield; Dennis P. Riley, Ballwin; Kenneth W. Ruettimann, St. Louis; A. John Solodar, University City; Thomas E. Waldman, Chesterfield, all of Mo.

[73] Assignee: Monsanto Company, St. Louis, Mo.

[21] Appl. No.: 173,010

[22] Filed: Dec. 27, 1993

[51] Int. Cl.$^6$ .............................................. C07C 263/04
[52] U.S. Cl. .................................... 560/345; 560/352
[58] Field of Search ...................... 560/338, 345, 353

[56] References Cited

U.S. PATENT DOCUMENTS

| | | |
|---|---|---|
| 2,829,095 | 4/1958 | Oda et al. . |
| 3,481,967 | 12/1969 | Ottmann et al. . |
| 4,022,791 | 5/1977 | Welch, Jr. . |
| 4,024,043 | 5/1977 | Dege et al. . |
| 4,116,889 | 9/1978 | Chlanda et al. . |
| 4,130,576 | 12/1978 | Hedaya et al. . |
| 4,178,309 | 12/1979 | Luetzow et al. . |
| 4,192,815 | 3/1980 | Sheludyakov et al. . |
| 4,297,501 | 10/1981 | Becker et al. . |
| 4,341,898 | 7/1982 | Milligan et al. . |
| 4,388,238 | 6/1983 | Heitkämper et al. . |
| 4,504,373 | 3/1985 | Mani et al. . |
| 4,567,294 | 1/1986 | Dressel et al. . |
| 4,582,923 | 4/1986 | Stammann et al. . |
| 5,189,205 | 2/1993 | McGhee et al. . |
| 5,221,443 | 6/1993 | Voss et al. . |

OTHER PUBLICATIONS

Belforte, A., et al., "Incoporation and Deoxygenation of Carbon Dioxide: A Metal-Assisted Facile Conversion of Carbon Dioxide and Primary Amines to Isocyanates", Chem. Ber., 121, 1891–97 (1988).

Hori, Y. et al., "New Organic Synthesis with DBU: Part 7. Synthesis of Carbonates and Carbamates with Carbon Dioxide Gas as the Starting Material", Chemistry Express, vol. 1, No. 4, pp. 224–227 (1986).

Schwesinger, R. and Schlemper, H., "Peralkylated Polyaminophasphazenes—Extremely Strong, Neutral Nitrogen Bases", Agnew. Chem. Int. Ed. Engl., 26, 11 (1987).

Schwesinger, R., "Extremely Strong, Non-ionic Bases: Synthesis and Applications", Chimia, 39, 9 (1985).

Stone, C. A. et al., "Structure-Activity Relationships in the Cyproheptadine Series", J. Med. Chem., 8, 829 (Nov. 1965).

Mani, K. N. et al., "Aquatech Membrane Technology for Recovery of Acid/Base Values from Salt Streams", Desalination, 68, 149–166 (1988).

McRae, W. A., "Electrodialysis", Kirk–Othmer Encyclopedia of Chemical Technology, vol. 8, 3rd Ed., pp. 726–738.

Johnson, W. L., "Electrodialysis with Bipolar Membranes", AIChE St. Louis Section, Symposium 92 and Chem. Show, Apr. 15, 1992.

Primary Examiner—José G. Dees
Assistant Examiner—Rosalynd Williams
Attorney, Agent, or Firm—Kenneth D. Goetz; Paul L. Passley; James C. Bolding

[57] ABSTRACT

A process for preparing isocyanates comprising contacting carbon dioxide and a primary amine in the presence of an aprotic organic solvent and a base selected from the group consisting of a phosphazene compound, an organic, nitrogenous base and mixtures thereof, wherein the organic, nitrogenous base selected from the group consisting of guanidine compounds, amidine compounds, tertiary amines and mixtures thereof to produce the corresponding ammonium carbamate salt, reacting the ammonium carbamate salt with an anhydride dehydrating agent to produce a product stream comprising the corresponding isocyanate, the aprotic organic solvent and the base salt derived from the anhydride, separating the base salt from the product stream, recovering and recycling the base, and regenerating and recycling the anhydride dehydrating agent.

49 Claims, 2 Drawing Sheets

PROCESS FOR PREPARING ISOCYANATES

BACKGROUND OF THE INVENTION

The invention relates to a process for preparing isocyanates. In one aspect, the invention relates to a new and useful process for preparing isocyanates from primary amines, carbon dioxide and an anhydride dehydrating agent.

Isocyanates, especially diisocyanates, are important commodity chemicals for use in applications such as preparation of urethane foam, urethane elastomers, coatings, insecticides, herbicides, and the like.

Commercially, the phosgenation of primary amines is by far the most widely used method for producing isocyanates. The use of phosgene, however, has several disadvantages. The phosgenation route is long, energy intensive and requires handling highly corrosive materials, e.g. hydrogen chloride and chlorine, and highly toxic reagents and intermediates, e.g. phosgene and chlorine. Furthermore, the phosgenation route requires use of process equipment which can withstand high temperatures and highly corrosive conditions resulting in increased capital costs.

One non-phosgene method for the preparation of isocyanates involves reaction of primary amines and $CO_2$ with a cobalt or manganese compound to produce metal carbamate complexes followed by reaction with an acyl halide in the presence of a solvent as is disclosed by A. Belforte et al., "Incorporation and Deoxygenation of Carbon Dioxide: A Metal-assisted Facile Conversion of Carbon Dioxide and Primary Amines To Isocyanates", Chem. Ber., 121, 1891-1897 (1988). However, the process described therein requires long reaction times and gives unsatisfactory yield of isocyanate for a commercially viable process.

Another non-phosgene route to isocyanates is found in U.S. Pat. No. 4,192,815 (Sheludyakov et al.) which discloses preparation of isocyanates by reacting a primary amine with $CO_2$ and hexamethyldisilazane in the presence of an acidic catalyst, e.g. $H_2SO_4$, followed by decomposition of the resulting silyl esters of carbamic acid in the presence of a dehydration agent. However, the process described therein requires long reaction times and is not commercially practicable.

A non-phosgene process for preparing isocyanates which is economical, commercially viable, and can produce isocyanates with high yield under mild reaction conditions and short reaction times is highly desirable.

SUMMARY OF THE INVENTION

It is an object of the invention to provide a process for preparing isocyanates. It is a further object of the invention to provide an efficient and economic process for preparing isocyanates that is commercially viable. It is a still further object of the invention to provide a process for preparing isocyanates which are not easily synthesized via phosgene routes.

According to the invention, a process for preparing an isocyanate is provided which comprises (a) contacting $CO_2$ and a primary amine in the presence of an aprotic organic solvent and a base selected from the group consisting of a phosphazene compound, an organic nitrogenous base and mixtures thereof, wherein the organic, nitrogenous base is selected from the group consisting of guanidine compounds, amidine compounds, tertiary amines and mixtures thereof, in a first reaction zone under reaction conditions of time and temperature sufficient to produce the corresponding ammonium carbamate salt, (b) passing the effluent stream of the first reaction zone into a second reaction zone and reacting the carbamate salt with a cyclic anhydride under reaction conditions of time and temperature sufficient to produce a first product stream containing the corresponding isocyanate, the aprotic organic solvent and the base salt derived from the anhydride, (c) passing the first product stream to a first separation zone and separating the base salt derived from the anhydride from the first product stream to form a second product stream comprising the isocyanate and aprotic organic solvent, (d) contacting in a third reaction zone the recovered base salt of (c) with an inorganic compound selected from the group consisting of alkali metal hydroxides, alkaline earth metal hydroxides, alkaline earth metal oxides, alkali metal carbonates and alkaline earth metal carbonates in an amount effective to liberate the base from the base salt and form a first effluent stream containing the base and corresponding alkali metal or alkaline earth metal salt, (e) introducing the first effluent stream into a second separation zone, separating the base from the first effluent stream and recycling the base to the first reaction zone, (f) introducing the thus recovered alkali metal or alkaline earth metal salt into an organic acid production zone to convert the alkali metal or alkaline earth metal salt into the organic acid corresponding to the anhydride, (g) optionally contacting the organic acid with a second solvent, (h) thermally dehydrating the organic acid in a thermal dehydration zone under conditions of temperature and pressure to remove water and regenerate the anhydride, and (i) recycling the anhydride to the second reaction zone, or when the second solvent is present and is different from the aprotic organic solvent, (i') (1) introducing the anhydride and the second solvent into a third separation zone to recover the second solvent, and (2) (i) recycling the anhydride to the second reaction zone or (ii) contacting the anhydride with the aprotic organic solvent and recycling the anhydride to the second reaction zone.

Further according to the invention, a process for preparing an isocyanate is provided which comprises (a) contacting $CO_2$ and a primary amine in the presence of an aprotic organic solvent and a base selected from the group consisting of a phosphazene compound, an organic nitrogenous base and mixtures thereof, wherein the organic, nitrogenous base is selected from the group consisting of guanidine compounds, amidine compounds, tertiary amines and mixtures thereof, in a first reaction zone under reaction conditions of time and temperature sufficient to produce the corresponding ammonium carbamate salt, (b) passing the effluent stream of the first reaction zone into a second reaction zone and reacting the carbamate salt with a cyclic anhydride under reaction conditions of time and temperature sufficient to produce a first product stream containing the corresponding isocyanate, the aprotic organic solvent and the base salt derived from the anhydride, (c) passing the first product stream to a first separation zone and separating the base salt derived from the anhydride from the first product stream to form a second product stream containing the isocyanate and the aprotic organic solvent, (d) introducing the recovered base salt of (c) into an electrodialysis zone to produce a base stream comprising the base and impurities and an organic acid stream wherein the organic acid corresponds to the anhydride, (e) introducing the base stream into a second separation zone, separating the base from the impurities to form a purified base stream, and recycling the base to the first reaction zone, (f) optionally contacting the organic acid with a second solvent, (g) thermally dehydrating the organic acid in a thermal dehydration zone under conditions of temperature and pressure to remove water and regenerate the anhydride, and (h) recycling the anhydride to the second reaction zone, or when the second solvent is present and is different from the aprotic organic solvent, (h') (1) introducing the anhydride and the second solvent into a third separation zone to recover the second solvent, and (2) (i) recycling the anhydride to the second reaction zone or (ii) contacting the anhydride with the aprotic organic solvent and recycling the anhydride to the second reaction zone.

DETAILED DESCRIPTION OF THE INVENTION

Figure 1:
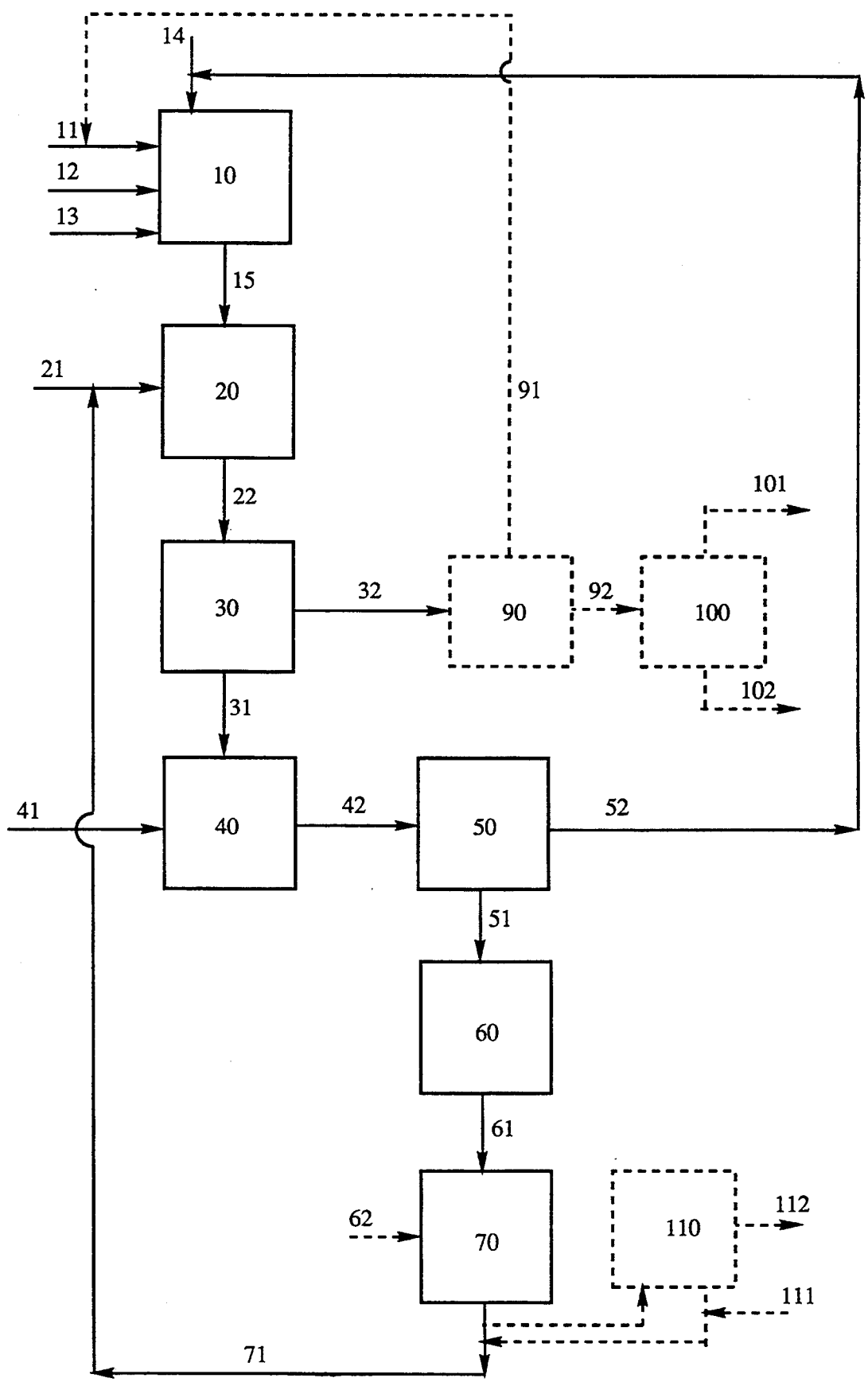
FIG. 1 is a schematic diagram illustrating a process for producing an isocyanate wherein the base and the anhydride are recycled according to the first embodiment of the invention.

A first embodiment of the invention, as illustrated in FIG. 1, relates to a process for preparing isocyanates comprising (a) contacting $CO_2$ (13) and a primary amine (12) in the presence of an aprotic organic solvent (11) and a base (14) selected from the group consisting of a phosphazene compound, an organic nitrogenous base and mixtures thereof, wherein the organic, nitrogenous base is selected from the group consisting of guanidine compounds, amidine compounds, tertiary amines and mixtures thereof, in a first reaction zone (10) under reaction conditions of time and temperature sufficient to produce the corresponding ammonium carbamate salt, (b) passing the effluent stream of the first reaction zone (15) into a second reaction zone (20) and reacting the carbamate salt with an anhydride (21) represented by the formula:

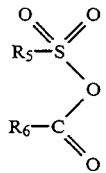

wherein $R_5$ and $R_6$ together form a cyclic anhydride or a cyclic anhydride containing a fused aromatic or fused cycloaliphatic ring, under reaction conditions of time and temperature sufficient to produce a first product stream (22) containing the corresponding isocyanate, the aprotic organic solvent and the base salt derived from the anhydride, (c) passing the first product stream to a first separation zone (30) and separating the base salt (31) derived from the anhydride from the first product stream to form a second product stream (32) comprising the isocyanate and aprotic organic solvent, (d) contacting in a third reaction zone (40) the recovered base salt of (c) with an inorganic compound (41) selected from the group consisting of alkali metal hydroxides, alkaline earth metal hydroxides, alkaline earth metal oxides, alkali metal carbonates and alkaline earth metal carbonates in an amount effective to liberate the base from the base salt and form a first effluent stream (42) containing the base and corresponding alkali metal or alkaline earth metal salt, (e) introducing the first effluent stream (42) into a second separation zone (50), separating the base (52) from the first effluent stream and recycling the base to the first reaction zone, (f) introducing the thus recovered alkali metal or alkaline earth metal salt (51) into an organic acid production zone (60) to convert the alkali metal or alkaline earth metal salt into the organic acid corresponding to the anhydride (61), (g) optionally contacting the organic acid with a second solvent (62), (h) thermally dehydrating the organic acid in a thermal dehydration zone (70) under conditions of temperature and pressure to remove water and regenerate the anhydride, and (i) recycling the anhydride (71) to the second reaction zone, or when the second solvent is present and is different from the aprotic organic solvent, (i') (1) introducing the anhydride and the second solvent into a third separation zone (110) to recover the second solvent (112), (2) (i) recycling the anhydride to the second reaction zone or (ii) contacting the anhydride with the aprotic organic solvent (111) and recycling the anhydride to the second reaction zone.

In one embodiment, the organic acid of (f) is produced by (1) contacting the recovered alkali metal or alkaline earth metal salt with an ion exchange resin, (2) introducing the alkali metal or alkaline earth metal salt into an electrodialysis zone to produce an alkali metal or alkaline earth metal hydroxide and the organic acid or (3) contacting the alkali metal or alkaline earth metal salt with a strong mineral or organic acid to produce the organic acid and an alkali metal or alkaline earth metal salt of the strong mineral or organic acid. In another embodiment, the second solvent is present and is immiscible with water and the thermal dehydration of (h) is conducted by heating the contents of the thermal dehydration zone to remove a mixture of water and the second solvent overhead, condensing the mixture of water and second solvent, phase separating the mixture of water and second solvent and refluxing the second solvent to the thermal dehydration zone. In a further embodiment, the thermal dehydration of (h) is conducted by heating the contents of the thermal dehydration zone in the presence of a desiccant. In a still further embodiment, the separation in the first separation zone of the base salt from the first product stream is conducted by: (1) filtering the base salt from the first product stream to recover the base salt and a filtrate comprising the aprotic organic solvent, the isocyanate and a trace amount of the base salt, and (2) (i) when the aprotic organic solvent is water immiscible, extracting the trace amount of base salt from the filtrate with water to produce the second product stream, or (ii) when the aprotic solvent is water miscible, performing a solvent exchange on the filtrate to replace the water miscible aprotic organic solvent with a water immiscible solvent and extracting with water or filtering the trace amount of base salt from the filtrate to produce the second product stream wherein the recovered base salt of (2) is combined with the recovered base salt of (1). In yet another embodiment, the second product stream (32) is introduced to a first fractionation zone (90) and fractionated to produce an aprotic organic solvent stream (91) and an isocyanate stream (92), and the aprotic organic solvent can be recycled. In yet a further embodiment, the isocyanate stream is introduced to a second fractionation zone (100) and fractionated to produce a purified isocyanate product stream (101) and a by-product stream (102).

Figure 2:
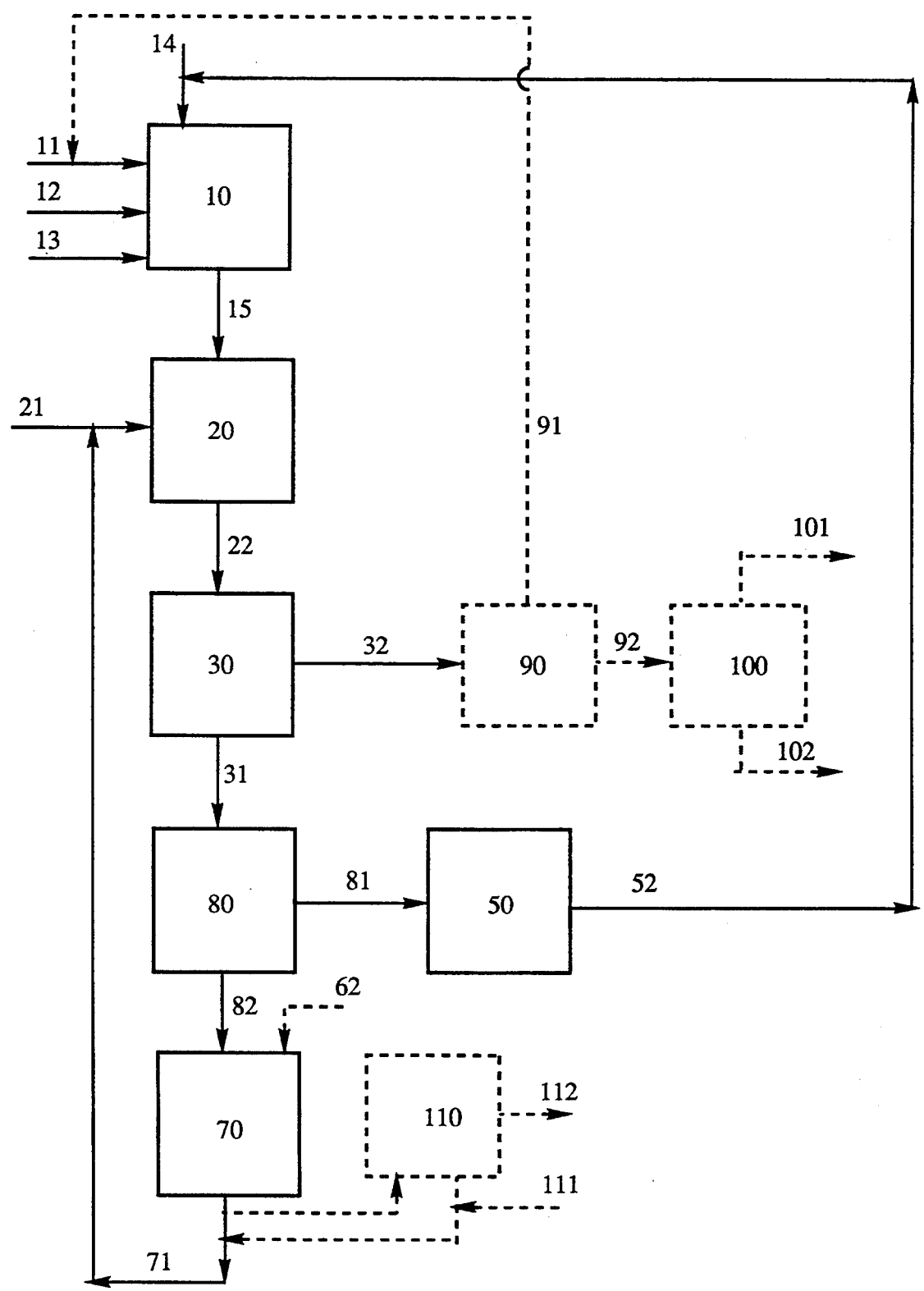
FIG. 2 is a schematic diagram illustrating a process for producing an isocyanate wherein the base and the anhydride are recycled according to the second embodiment of the invention.

A second embodiment of the invention, as illustrated in FIG. 2, relates to a process for preparing isocyanates comprising (a) contacting $CO_2$ (13) and a primary amine (12) in the presence of an aprotic organic solvent (11) and a base (14) selected from the group consisting of a phosphazene compound, an organic nitrogenous base and mixtures thereof, wherein the organic, nitrogenous base is selected from the group consisting of guanidine compounds, amidine compounds, tertiary amines and mixtures thereof, in a first reaction zone (10) under reaction conditions of time and temperature sufficient to produce the corresponding ammonium carbamate salt, (b) passing the effluent stream of the first reaction zone (15) into a second reaction zone (20) and reacting the carbamate salt with an anhydride (21) represented by the formula:

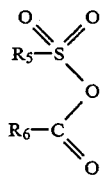

wherein $R_5$ and $R_6$ together form a cyclic anhydride or a cyclic anhydride containing a fused aromatic or fused cycloaliphatic ring, under reaction conditions of time and temperature sufficient to produce a first product stream (22) containing the corresponding isocyanate, the aprotic organic solvent and the base salt derived from the anhydride, (c) passing the first product stream to a first separation zone (30) and separating the base salt (31) derived from the anhydride from the first product stream to form a second product stream (32) containing the isocyanate and the aprotic organic solvent, (d) introducing the recovered base salt of (c) into an electrodialysis zone (80) to produce a base stream (81) and an organic acid stream (82) wherein the organic acid corresponds to the anhydride, (e) introducing the base stream into a second separation zone (50), recovering the base to form a purified base stream (52), and recycling the base to the first reaction zone, (f) optionally contacting the organic acid with a second solvent (62), (g) thermally dehydrating the organic acid in a thermal dehydration zone (70) under conditions of temperature and pressure to remove water and regenerate the anhydride, and (h) recycling the anhydride (71) to the second reaction zone, or when the second solvent is present and is different from the aprotic organic solvent, (h') (1) introducing the anhydride and the second solvent into a third separation zone (110) to recover the second solvent (112), and (2) (i) recycling the anhydride to the second reaction zone or (ii) contacting the anhydride with the aprotic organic solvent (111) and recycling the anhydride to the second reaction zone.

In one embodiment, the second solvent is present and is immiscible with water and the thermal dehydration of (h) is conducted by heating the contents of the thermal dehydration zone to remove a mixture of water and the second solvent overhead, condensing the mixture of water and second solvent, phase separating the mixture of water and second solvent and refluxing the second solvent to the thermal dehydration zone. In another embodiment, the thermal dehydration of (h) is conducted by heating the contents of the thermal dehydration zone in the presence of a desiccant. In a further embodiment, the separation in the first separation zone of the base salt from the first product stream is conducted by (1) filtering the base salt from the first product stream to recover the base salt and a filtrate comprising the aprotic organic solvent, the isocyanate and a trace amount of the base salt, and (2) (i) when the aprotic organic solvent is water immiscible, extracting the trace amount of base salt from the filtrate with water to produce the second product stream, or (ii) when the aprotic solvent is water miscible, performing a solvent exchange on the filtrate to replace the water miscible aprotic organic solvent with a water immiscible solvent and extracting with water or filtering the trace amount of base salt from the filtrate to produce the second product stream wherein the recovered base salt of (2) is combined with the recovered base salt of (1). In a still further embodiment, the second product stream (32) is introduced to a first fractionation zone (90) and fractionated to produce an aprotic organic solvent stream (91) and an isocyanate stream (92), and the aprotic organic solvent can be recycled. In yet another embodiment, the isocyanate stream is introduced to a second fractionation zone (100) and fractionated to produce a purified isocyanate product stream (101) and a by-product stream (102).

The isocyanates made according to this invention are readily recoverable and well suited for use in preparation of urethane foams, elastomers and coatings, insecticides, and herbicides.

The isocyanates produced by the process of the invention can be represented by the formula:

$$R_2-N=C=O$$

wherein $R_2$ is selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, a radical represented by the formula:

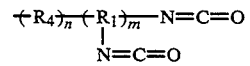

a radical represented by the formula:

$$-R_4-N=C=O$$

a radical represented by the formula:

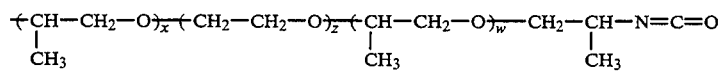

or isocyanates produced by the process of the invention can be represented by the formula:

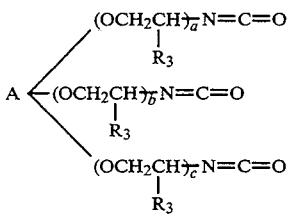

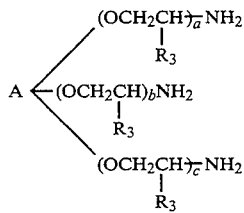

wherein $R_1$ and $R_4$ are independently selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, $R_3$ is hydrogen or methyl, $x+w$ represents an integer from about 2 to about 70, z represents an integer from 0 to about 90, $x+w+z$ represents an integer from about 2 to about 100, a, b and c independently represent an integer from about 2 to about 30, and A represents a trihydric alcohol initiator such as glycerine or trimethylolpropane. In addition, $R_2$ may contain nonnucleophilic functional groups which do not react preferentially with the anhydride dehydrating agent. Examples of suitable functional groups include esters, amides, urethanes, carbonates, and the like, and salts thereof.

Examples of isocyanates produced by the process of the invention include, but are not limited to, cyclohexyl isocyanate, octyl isocyanate, 1,4-cyclohexyl diisocyanate, phenyl isocyanate, phenylalanine methyl ester isocyanate, glycine benzyl ester isocyanate, alanine benzyl ester isocyanate, phenylalanine ethyl ester isocyanate, leucine ethyl ester isocyanate, valine ethyl ester isocyanate, β-alanine ethyl ester isocyanate, glutamic acid diethyl ester isocyanate, hydrogenated toluene diisocyanate, hexamethylene diisocyanate, 4-isocyanatomethyl-1,8-octanediisocyanate, the diisocyanate of Jeffamine ® D-400, and the like, and mixtures thereof.

The ammonium salt of the carbamate anion is prepared in solution in the presence of an organic, nitrogenous base. The reaction between the primary amine and carbon dioxide to form the ammonium carbamate salt may be represented by the equation (1).

$$RNH_2 + CO_2 + Base \rightleftharpoons RNHCO_2^- {}^+H\,Base \qquad (1)$$

The result of the reaction of the ammonium carbamate salt with the anhydride dehydrating agent may be represented by the equation (2).

$$RNHCO_2^- {}^+H\,Base + \text{"Dehydrating Agent"} \rightarrow R-N=C=O + salt \qquad (2)$$

The primary amines for use in the process of the invention are selected from the group consisting of compounds represented by the formula $R-NH_2$, polyoxyalkylene diamines represented by the formula:

wherein R is selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, a radical represented by the formula:

$$-\!\!+\!\!R_4\!\!\}_{\!n}\!\!+\!\!R_1\!\!\}_{\!m}\!\!-\!\!NH_2$$
$$\quad\quad\quad\quad |$$
$$\quad\quad\quad\quad NH_2$$

and a radical represented by the formula:

$$-R_4-NH_2,$$

wherein $R_1$, $R_3$, $R_4$, a, b, c, m, n, w, x, z and A are as defined above. Suitable primary amines include diamines and polyamines. In addition, R may contain nonnucleophilic functional groups which do not react preferentially with the anhydride dehydrating agent. Examples of suitable functional groups include esters, amides, urethanes, carbonates, and the like, and salts thereof.

Examples of primary amines which can be employed in the process of the invention include cyclohexyl amine, octyl amine, 1,4-diaminocyclohexane, aniline, methyl amine, ethyl amine, n-propyl amine, isopropyl amine, n-butyl amine, isobutyl amine, t-butyl amine, n-pentyl amine, isopentyl amine, n-hexyl amine, n-octyl amine, benzyl amine, phenylalanine methyl ester hydrochloride salt, glycine benzyl ester p-toluene sulphonic acid salt, alanine benzyl ester hydrochloride salt, phenyl alanine ethyl ester hydrochloride salt, leucine ethyl ester hydrochloride salt, valine ethyl ester hydrochloride salt, β-alanine ethyl ester hydrochloride salt, glutamic acid ethyl ester hydrochloride salt, 2,6-methylcyclohexyldiamine, 2,4-methylcyclohexyldiamine, n-hexyldiamine, 4,4'-methylene diphenyl amine, hexamethylene diamine, 4-aminomethyl-1,8-octanediamine, polyoxyalkylenediamines such as those available from Texaco Chemical Company under the trademark Jeffamine ® including D-230 (approximate molecular weight=230), D-400 (approximate molecular weight=400), D-2000 (approximate molecular weight=2,000), D-4000 (approximate molecular weight=4,000), ED-600 (approximate molecular weight=600), ED-900 (approximate molecular weight=900), ED-2001 (approximate molecular weight=2,000), ED-4000 (approximate molecular weight=4,000) and ED-6000 (approximate molecular weight=6,000), polyoxyalkylene triamines such as $$H_2N\!\!+\!\!\underset{CH_3}{CH}\!\!-\!\!CH_2\!\!-\!\!O\!\!\}_x\!\!+\!\!CH_2\!\!-\!\!CH_2\!\!-\!\!O\!\!\}_z\!\!+\!\!\underset{CH_3}{CH}\!\!-\!\!CH_2\!\!-\!\!O\!\!\}_w\!\!-\!\!CH_2\!\!-\!\!\underset{CH_3}{CH}\!\!-\!\!NH_2$$

and polyoxyalkylene triamines represented by the formula:

those available from Texaco Chemical Company under the trademark Jeffamine ® including T-403 (approximate molecular weight=440), T-3000 (approximate molecular weight=3,000) and T-5000 (approximate molecular weight=5,000), tetraethylene pentamine, diethylene triamine, trimethylene tetramine, pentaethylene hexamine, and the like, and mixtures thereof.

Applicable solvents for use in the process of the invention are aprotic organic solvents. Both polar and non-polar aprotic organic solvents, as well as mixtures thereof, may be used in the process of the invention. As utilized herein, the phrase "polar aprotic organic solvent" means an aprotic organic solvent having a dielectric constant measured at 25° C. of greater than about 10 as reported in Reichardt, C., "Solvents and Solvent Effects in Organic Chemistry," 2nd ed., VCH Verlagsgesellschaft, Weinheim, (1988), Table A-1. Other methods for determining dielectric constants are known and suitable polar aprotic organic solvents are those having a dielectric constant greater than that of tetrahydrofuran utilizing any of such methods.

Examples of non-polar aprotic organic solvents which can be employed in the process of the invention include dichloromethane, toluene, tetrahydrofuran, o-dichlorobenzene, monochlorobenzene, triethylamine and the like, and mixtures thereof.

Examples of polar aprotic organic solvents which can be employed in the process of the invention include dimethyl formamide, N-methyl-2-pyrrolidone, N,N-dimethyl acetamide, dimethyl sulfoxide, acetonitrile, propionitrile, sulfolane, pyridine and the like, and mixtures thereof.

Although not specifically required, it is preferred to utilize the same solvent to carry out the reactions in the first and second reaction zones of the present invention in order to avoid additional process equipment for recovering additional solvents.

To obtain high selectivities and yields for the desired isocyanates, a phosphazene compound, an organic, nitrogenous base or mixtures thereof is employed as the base in the process of the invention. The phrase "organic, nitrogenous base" as used herein refers to a base other than the phosphazene compound which is utilized in addition to the reactant primary amine. Applicable organic, nitrogenous bases for use in the process of the invention include guanidine compounds, amidine compounds, tertiary amines and mixtures of any two or more thereof.

The phosphazene compounds of the invention are compounds represented by the formula:

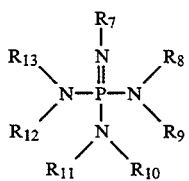

wherein $R_7$, $R_8$, $R_9$, $R_{10}$, $R_{11}$, $R_{12}$ and $R_{13}$ are independently selected from the group consisting of alkyl, aryl, alkaryl, aralkyl and cycloalkyl radicals having 1 to about 22 carbon atoms; or one of $R_8$ or $R_9$ together with one of $R_{10}$ or $R_{11}$, one of $R_{12}$ or $R_{13}$ together with one of $R_{10}$ or $R_{11}$, and $R_7$ together with one of $R_8$ or $R_9$ or one of $R_{12}$ or $R_{13}$ independently form a nitrogen-containing heterocycle; or $R_8$ together with $R_9$, $R_{10}$ together with $R_{11}$, and $R_{12}$ together with $R_{13}$ independently represent a radical represented by the formula:

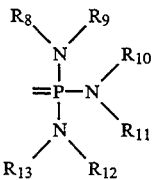

wherein $R_8$, $R_9$, $R_{10}$, $R_{11}$, $R_{12}$ and $R_{13}$ are as defined above.

Examples of phosphazene compounds which can be employed in the process of the invention include, but are not limited to, t-butyliminotris(dimethylamino)-phosphorane ($P_1$-tBu), 1-t-butyl-4,4,4-tris(dimethylamino)-2,2-bis-[tris(dimethylamino) phosphoranylideneamino]-2λ,4λ-catenadi (phosphazene) ($P_4$-tBu), 2-t-butylimino-2-diethylamino-1,3-dimethyl-perhydro-1,3,2-diazaphosphorane (BEMP), t-butyliminotris (diethylamino) phosphorane, 2-t-octylimino-2-diethylamino-1,3-dimethyl-perhydro-1,3,2-diazaphosphorane, and the like, and mixtures of any two or more thereof.

The guanidine compounds of the invention are compounds represented by the formula:

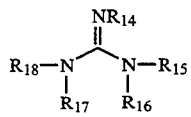

wherein $R_{14}$, $R_{15}$, $R_{16}$, $R_{17}$ and $R_{18}$ are independently selected from the group consisting of alkyl, aryl, alkaryl, aralkyl and cycloalkyl radicals having 1 to about 22 carbon atoms; or $R_{14}$ together with one of $R_{15}$, $R_{16}$, $R_{17}$ or $R_{18}$, $R_{15}$ and $R_{16}$, and $R_{17}$ and $R_{18}$ independently form a nitrogen-containing heterocycle.

The amidine compounds of the invention are compounds represented by the formula:

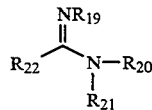

wherein $R_{19}$, $R_{20}$, $R_{21}$ and $R_{22}$ are independently selected from the group consisting of alkyl, aryl, alkaryl, aralkyl and cycloalkyl radicals having 1 to about 22 carbon atoms; or $R_{19}$ together with $R_{20}$ or $R_{21}$ and $R_{22}$ together with $R_{20}$ or $R_{21}$ independently form a nitrogen-containing heterocycle.

Examples of organic, nitrogenous bases which can be employed in the process of the invention include triethylamine, diethyl isopropylamine, trimethylamine, tetramethyl guanidine (TMG), cyclohexyl-tetramethyl guanidine (CyTMG), butyltetraethyl guanidine (n-BTEG), cyclohexyl-tetraethyl guanidine (CyTEG), tetraethyl guanidine (TEG), t-butyl-tetraethyl guanidine (t-BTEG), 7-methyl-1,5,7-triazabicyclo[4.4.0]dec-5-ene (MTBD), t-butyl-dimethyl formamidine (t-BDMF), t-butyldimethyl acetamidine (t-BDMA), 1,5-diazabicyclo[4.3.0]non-5-ene (DBN), 1,8-diazabicyclo[5.4.0] undec-7-ene (DBU) and the like, and mixtures of any two or more thereof. The currently preferred organic, nitrogenous base is triethylamine because of cost and excellent results obtained therewith.

The amount of base, i.e., phosphazene compound, organic, nitrogenous base or mixture thereof, utilized in the process of the invention will depend upon the particular embodiment of the process.

The amount of base can be conveniently expressed in terms of a ratio based on the number of equivalents of amine in the primary amine charged. Broadly, the ratio of the number of moles of base to the number of equivalents of amine in the primary amine will be about 1:1 to about 20:1, preferably about 2:1 to about 10:1, and most preferably about 2:1 to about 4:1. The base can be completely charged at the beginning of the process, or a portion may be charged at the beginning of the process and the remainder charged at any time prior to the reaction of the ammonium carbamate salt with the anhydride.

Applicable anhydride dehydrating agents for use in the process of the invention can be represented by the formula:

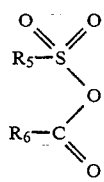

wherein $R_5$ and $R_6$ together form a cyclic anhydride or a cyclic anhydride containing a fused aromatic or fused cycloaliphatic ring. The preferred fused aromatic rings are phenyl and naphthyl and the preferred fused cycloaliphatic rings have about 5 to about 8 carbon atoms. The preferred cyclic anhydrides have 3 to about 5 carbon atoms including the carbonyl carbon, i.e. preferably $R_5$ and $R_6$ together have a total number of carbon atoms from 2 to about 4.

The cyclic anhydride, or the fused aromatic or fused cycloaliphatic ring of the cyclic anhydride can be substituted or unsubstituted. Examples of substituents include, but are not limited to, alkyl, halogen, —$NO_2$, and the like, and combinations thereof. Halogen, as used herein, is selected from the group consisting of fluorine, chlorine, bromine and iodine, preferably fluorine and chlorine.

Examples of suitable anhydride dehydrating agents include 2-sulfobenzoic anhydride, 2-sulfocyclohexanoic anhydride, 2-sulfonaphthoic anhydride, 2-sulfocyclooctanoic anhydride, and the like, and mixtures thereof. The currently preferred anhydride dehydrating agent is 2-sulfobenzoic anhydride because of the high yields achievable with this compound under mild reaction conditions.

The amount of anhydride dehydrating agent can be conveniently expressed in terms of a ratio based on the number of equivalents of amine in the primary amine charged. Broadly, the ratio of the number of moles of anhydride dehydrating agent to the number of equivalents of amine in the primary amine will be about 0.4:1 to about 10:1, preferably about 1:1 to about 5:1 and most preferably about 1:1 to about 2:1.

The reaction between the primary amine and carbon dioxide is conducted under a $CO_2$ atmosphere. The pressure of $CO_2$ during this reaction is 0 psig (atmospheric pressure) to about 1000 psig, preferably 0 psig to about 150 psig, and most preferably 0 psig to about 80 psig. It is preferred to charge the $CO_2$ to the reaction vessel containing the primary amine below the liquid level in the reaction vessel. Although not specifically required, it is preferred to conduct the reaction of ammonium carbamate salt with anhydride dehydrating agent under a $CO_2$ atmosphere. However, the reaction of ammonium carbamate salt with anhydride dehydrating agent can be conducted under any inert atmosphere, e.g. nitrogen, argon or air, provided the atmosphere is substantially dry. A substantially dry atmosphere is critical because water will react with the anhydride dehydrating agent. The pressure during this reaction is 0 psig to about 1000 psig, preferably 0 psig to about 150 psig, and most preferably 0 psig to about 80 psig.

The temperature and time used in the first and second reaction zones will depend on the particular reaction involved. For the reaction of primary amine with $CO_2$, the temperature is about $-78°$ C. to about 100° C., preferably about $-40°$ C. to about 40° C., and most preferably about $-20°$ C. to about 30° C. The time will broadly be the time required to achieve complete mixing of reactants to about 4 hours, preferably about 5 minutes to about 1 hour. For the reaction of ammonium carbamate salt with anhydride dehydrating agent, the temperature is about $-78°$ C. to about 100° C., preferably about $-40°$ C. to 40° C., and most preferably about $-30°$ C. to about 10° C. The time will broadly be the time required to achieve complete addition and mixing of the reactants to about 4 hours, preferably about 1 minute to about 1 hour.

Although not currently preferred, the reaction of primary amine with $CO_2$ in the first reaction zone and the reaction of ammonium carbamate salt with anhydride dehydrating agent in the second reaction zone can be conducted in the same process vessel or zone depending on the mode of operation used in the processes of the invention. For example, if the first and second reactions are conducted in the batch mode it is preferred to conduct the first and second reactions in the same process vessel or zone.

The desired isocyanates produced by the process of the invention can be recovered by any conventional means known in the art, such as that disclosed in the examples or described herein.

When the first product stream contains free base, i.e. excess base is utilized during the formation of the ammonium carbamate salt or the isocyanate, it is currently preferred to remove the excess base from the first product stream prior to separating the base salt from the first product stream. The excess base can be removed by any conventional method known to those of ordinary skill in the art.

The separation of the base salt from the first product stream in the first separation zone (30) can be by any conventional method known to those of ordinary skill in the art. For example, the separation can be done using a physical separation technique, such as filtration or screening, to separate the base salt from the first product stream. Other techniques may be used in conjunction with the physical separation technique, e.g. washing, extraction and solvent exchange, depending on the characteristics of the base salt, aprotic organic solvent, isocyanate or other solvent used, such as solubility in water.

The currently preferred methods for conducting the separation of the base salt from the first product stream for operability reasons include: (1) filtering the base salt from the first product stream to recover the base salt and a filtrate comprising the aprotic organic solvent, the isocyanate and a trace amount of the base salt, and (2) (i)

when the aprotic organic solvent is water immiscible, extracting the trace amount of base salt from the filtrate with water to produce the second product stream, or (ii) when the aprotic solvent is water miscible, performing a solvent exchange on the filtrate to replace the water miscible aprotic organic solvent with a water immiscible solvent and extracting with water or filtering the trace amount of base salt from the filtrate to produce the second product stream wherein the recovered base salt of (2) is combined with the recovered base salt of (1).

Solvent exchange, as used herein, comprises contacting the filtrate with a second solvent, i.e. a water immiscible solvent, followed by removal of the first solvent, i.e. an aprotic organic solvent, by any conventional method known to those of ordinary skill in the art, e.g. distillation. Examples of suitable water immiscible solvents include, but are not limited to, chlorobenzene, octane, xylene, and the like. The temperature utilized in the solvent exchange operation will depend on the particular solvents used and will be clear to those of ordinary skill in the art.

According to the first embodiment, a third reaction zone (40) is utilized to liberate the base from the base salt derived from the anhydride and form the corresponding alkali metal or alkaline earth metal salt of the base salt. The base is liberated by the addition of an effective amount of an inorganic compound (41) to the third reaction zone and contacting the base salt and the inorganic compound under suitable conditions of temperature and time sufficient to liberate the base. Depending on the particular base salt, it may be necessary to contact the base salt with water prior to liberation of the base.

Suitable inorganic compounds for use in the invention are selected from the group consisting of alkali metal hydroxides, alkaline earth metal hydroxides, alkaline earth metal oxides, alkali metal carbonates and alkaline earth metal carbonates. Examples of suitable inorganic compounds include, but are not limited to, sodium hydroxide, potassium hydroxide, lithium hydroxide, calcium hydroxide, magnesium hydroxide, calcium oxide, magnesium oxide, sodium carbonate, potassium carbonate, calcium carbonate, magnesium carbonate, and the like, and mixtures thereof. The currently preferred inorganic compounds are sodium hydroxide and calcium hydroxide because of economics and effectiveness.

The effective amount of inorganic compound can be based on the ratio of neutralizing equivalents of the inorganic compound to moles of the base salt. The ratio of the neutralizing equivalents of inorganic compound to the moles of base salt is from about 1:1 to about 2:1, preferably about 1:1 to about 1.4:1, and most preferably about 1:1 to about 1.2:1.

The temperature and time used in the third reaction zone will depend on the particular reaction involved. The reaction temperature will generally be about 10° C. to about 100° C., preferably about 20° C. to about 30° C. The time will generally be the time required for neutralization. The reaction between the base salt and the inorganic compound is preferably conducted under an inert atmosphere, e.g. nitrogen or argon.

According to either the first or second embodiments, the second separation zone (50) is utilized to separate the base from the first effluent stream (42) and produce a purified base stream (52), which is recycled to the first reaction zone, and a recovered alkali metal or alkaline earth metal salt stream (51). The separation of the base from the first effluent stream in the second separation zone (50) can be by any conventional method known to those of ordinary skill in the art. Examples of methods for separating the base from the first effluent stream include steam distillation which can optionally be followed by a drying distillation, extraction if the extractant used is the same as the solvent used in the carbamate formation, and extraction followed by distillation if the extractant used is different from the solvent used in the carbamate formation. The currently preferred method for separating the base from the alkali metal or alkaline earth metal salt, particularly when the base is triethyl amine, is by a steam distillation technique under suitable conditions of temperature and pressure followed by a second distillation to remove water.

The temperature and pressure used in the second separation zone will depend on the particular separation method utilized and the base to be separated.

According to the first embodiment, the recovered alkali metal or alkaline earth metal salt (51) is introduced into an organic acid production zone (60) to convert the salt into the organic acid corresponding to the anhydride (61). The organic acid can be produced from the salt by any conventional method known to those of ordinary skill in the art. Examples of methods for producing the organic acid from the salt include, but are not limited to, the following.

A first method for producing the organic acid is by contacting the recovered alkali metal or alkaline earth metal salt with an ion exchange resin. Suitable ion exchange resins are well known to those of ordinary skill in the art. As used herein, the ion exchange resins applicable for the process of the invention are cation exchange resins in proton form such as strong acid sulfonated polystyrene resins in the $H^+$ form. Examples of suitable ion exchange resins include, but are not limited to, Amberlite® IR-120 ($H^+$) available from the Rohm & Haas Company and the Dowex® 50X series resins available from the Dow Chemical Company. The ion exchange resins can be in any conventional form known to those of ordinary skill in the art, such as pellets, membranes and packed beds. Periodically, the ion exchange resins which have been used to convert the salt into the organic acid are regenerated by contacting the resin with a mineral acid capable of protonating the ion exchange resin and regenerating the acid form of the resin. Regeneration of ion exchange resins is well known to those of ordinary skill in the art. Examples of mineral acids include, but are not limited to, sulfuric acid, hydrochloric acid, nitric acid, phosphoric acid, and the like, and mixtures thereof. The currently preferred mineral acids are sulfuric acid and hydrochloric acid because of excellent results achievable therewith. The product of the regeneration will be the alkali metal or alkaline earth metal salt of the mineral acid.

The alkali metal or alkaline earth metal salt of the mineral acid can optionally be introduced into an electrodialysis zone to produce a mineral acid stream and an alkali metal or alkaline earth metal hydroxide stream. Both recovered streams can then be recycled, i.e. the mineral acid can be recycled to regenerate the ion exchange resin and the alkali metal or alkaline earth metal hydroxide can be recycled to the third reaction zone.

A second method for producing the organic acid is by introducing the alkali metal or alkaline earth metal salt into an electrodialysis zone to produce the alkali metal or alkaline earth metal hydroxide and the organic acid. Electrodialysis, as used herein, is a process for moving ions across a membrane from one solution to another under the influence of a direct electric current such as is described in the Kirk-Othmer Encyclopedia of Chemical Technology, Vol. 8, 3rd edition, pp. 726–738, and in U.S. Pat. No. 4,504,373, which are incorporated by reference herein. Electrodialysis, as defined herein, includes electrohydrolysis. An electrodialysis apparatus is fundamentally an array of alternating anion-selective and cation-selective membranes terminated by electrodes. The membranes are separated from each other by gaskets which form fluid compartments. Compartments that have anion-selective membranes on the side facing the anode are electrolyte-depletion compartments. The remaining compartments are electrolyte-enrichment compartments. The enrichment and depletion compartments also alternate through the array. Holes in the gaskets and membranes register with each other to provide two pairs of internal hydraulic manifolds to carry fluid into and out of the compartments, one pair communicating with the electrolyte-depletion compartments and the other with the electrolyte-enrichment compartments. A contiguous group of two membranes and their associated two fluid compartments is called a cell pair. A group of cell pairs and their associated end electrodes are called a stack or pack. Generally one hundred to several hundred cell pairs are arranged in a single stack, with the number of cell pairs dependent on the electrodialysis capacity desired, the uniformity of flow distribution achieved among the several compartments of the same class in a stack and the maximum total direct current potential desired.

Commercial membranes are well known to those of ordinary skill in the art. Anion-selective membranes are strongly, mildly or weakly basic anion permselective membranes and include, but are not limited to, those available from Ionics Inc., Watertown, Mass., and sold as Ionics 204-UZL-386, those available from Asahi Glass Company under the trade name Selemion® AMV or ASV anion permselective membranes, and the like. Cation-selective membranes are weakly acidic or strongly acidic cation permselective membranes and include, but are not limited to, those available from E.I. dupont de Nemours & Co., Inc. under the trade name Nafion® acidic fluorocarbon membranes such as Nafion® 110, 117, 324 or 417, and the like. Commercial membranes typically have thicknesses of approximately 0.15–0.6 mm. The compartments between the membranes typically have thicknesses of approximately 0.5–2 mm. The thickness of a cell pair is therefore approximately 1.3–5.2 mm, generally about 3.2 mm such that one hundred cell pairs would generally have a combined thickness of 320 mm. The effective area of a cell pair for current conduction is generally about 0.2–2 $m^2$.

A currently preferred electrodialysis process utilizes bipolar membranes, i.e. a membrane that can split water directly into its $H^+$ and $OH^-$ ions under an applied electric potential. Examples of bipolar membranes include, but are not limited to, those of the type described in U.S. Pat. Nos. 2,829,095, 4,024,043 (single film bipolar membrane) and 4,116,889 (cast bipolar membrane), which are incorporated by reference herein. The way in which a bipolar membrane is used to split a salt into its acid and base components is to integrate it with monopolar, ion-selective membranes such as those described above. By pairing the cationic portion of the salt with the hydroxyl ion produced by the bipolar membrane, a base product is formed. Similarly, pairing the anionic portion of the salt with the hydrogen ion produces an acid product. To take advantage of the bipolar membrane's water-splitting efficiency, multiples of the three-compartment cells are arranged using the same set of electrodes, resulting in a stack of thin membranes and solution compartments comprising 100 or more cells. Other alternate cell arrangements can be utilized in which the bipolar electrode is paired in an alternating manner only with cation-selective or anion-selective membranes resulting in two-compartment cells. The use of bipolar electrodes is described in Mani, K. N. et al. (Aquatech Systems, Allied-Signal, Inc.), "Aquatech Membrane Technology for Recovery of Acid/Base Values from Salt Streams", *Desalination*, 68, 149–166 (1988) and Johnson, W. L. (WSI Technologies, Inc.), "Electrodialysis with Bipolar Membranes", Symposium "92" and Chem Show, St. Louis, Mo. Section, American Institute of Chemical Engineers, Apr. 15, 1992, which are incorporated by reference herein.

In a preferred embodiment, the alkali metal or alkaline earth metal hydroxide product of the electrodialysis is recycled to the third reaction zone.

A third method for producing the organic acid is a neutralization method comprising contacting the alkali metal or alkaline earth metal salt with a strong mineral or organic acid, preferably a strong mineral acid, to produce the organic acid corresponding to the anhydride and an alkali metal or alkaline earth metal salt of the strong mineral or organic acid. As used herein, the term "strong mineral or organic acid" means an acid which is capable of protonating the alkali metal or alkaline earth metal salt and forming the organic acid corresponding to the anhydride. Examples of strong mineral acids include, but are not limited to, sulfuric acid, hydrochloric acid, nitric acid, and the like, and mixtures thereof. The currently preferred mineral acids are sulfuric and hydrochloric acid because of excellent results achievable therewith. Examples of strong organic acids include, but are not limited to, benzene sulfonic acid, trifluoromethane sulfonic acid, and the like, and mixtures thereof.

The neutralization is conducted at suitable conditions of temperature and time sufficient to produce the organic acid corresponding to the anhydride. The temperature and time used in the neutralization will depend on the particular salt being neutralized and the particular strong mineral or organic acid used. The reaction temperature will generally be about 10° C. to about 100° C., preferably about 20° C. to about 30° C. The time will generally be the time required for neutralization. The neutralization is preferably conducted under an inert atmosphere, e.g. nitrogen or argon.

When the alkali metal or alkaline earth metal salt of the strong mineral or organic acid precipitates during the neutralization, the salt can be removed prior to addition of the second solvent. When the organic acid produced by the neutralization is contacted with the second solvent prior to the thermal dehydration, the alkali metal or alkaline earth metal salt of the strong mineral or organic acid is (1) separated from the organic acid prior to the thermal dehydration or (2) separated from the anhydride prior to recycling the anhydride to the second reaction zone. When the thermal dehydration is conducted in the absence of the second solvent, the effluent stream of the thermal dehydration zone is contacted with a second solvent and the alkali metal or alkaline earth metal salt of the strong mineral or organic acid is separated from the anhydride prior to recycling the anhydride to the second reaction zone. The removal of the salt of the strong mineral or organic acid can be done by any conventional method known to those of ordinary skill in the art. The currently preferred separation method is filtration due to economics and operability.

The second solvent which can be optionally contacted with the organic acid prior to the thermal dehydration or with the anhydride after the thermal dehydration is an aprotic organic solvent, and preferably a water immiscible solvent. The second solvent can also be utilized in the solvent exchange step of the separation in the first separation zone when a solvent exchange is necessary. The selection of the second solvent will be dependent on the organic acid or anhydride being contacted with the second solvent. Examples of the second solvent include, but are not limited to, toluene, xylene, chlorobenzene, o-dichlorobenzene, cumene and mixtures thereof. The currently preferred second solvent is xylene or cumene because of economics and generally good results obtained therewith.

According to either the first or second embodiments, the thermal dehydration zone (70) is utilized to heat the organic acid under conditions of temperature and pressure to physically remove water and produce the corresponding anhydride. The temperature and pressure used in the thermal dehydration zone will depend on the particular dehydration method utilized and the organic acid to be dehydrated. Generally, the temperature will generally be about 95° C. to about 200° C., preferably about 120° C. to about 170° C.

The thermal dehydration can be accomplished by any conventional method known to those of ordinary skill in the art. Two particularly useful methods for thermally dehydrating the organic acid involve (1) the distillation of a water/solvent mixture, removal of water and reflux of solvent, and (2) the removal of water released upon heating the organic acid using a desiccant. According to method (1), when a second solvent is present with the organic acid and the second solvent is water immiscible, the thermal dehydration is accomplished by heating the contents of the thermal dehydration zone to remove a mixture of water and the second solvent overhead, condensing the mixture of water and second solvent, phase separating the mixture of water and second solvent and refluxing the second solvent to the thermal dehydration zone. According to method (2), the thermal dehydration is conducted by heating the contents of the thermal dehydration zone in the presence of a desiccant.

Examples of suitable desiccants include, but are not limited to, molecular sieves such as types 4A, 5A and 13X available from the Union Carbide Corporation, zinc chloride, calcium chloride, silica gel, activated alumina, and mixtures thereof. The currently preferred desiccant is a molecular sieve.

Although not currently preferred, the thermal dehydration can also be conducted in the presence of a macroreticular hydrophobic ion exchange resin. Examples of macroreticular hydrophobic ion exchange resins suitable for use in the thermal dehydration include, but are not limited to, Amberlyst 15, and Amberlyst XN-1010 of the Rohm & Haas Co.

Although not currently preferred, the organic acid production and thermal dehydration operations can be conducted in the same process vessel or zone depending on the method selected for producing the organic acid. For example, when the organic acid is produced by neutralization, the organic acid production and thermal dehydration can be done in the same zone.

According to either the first or second embodiments, the anhydride stream (71) from thermal dehydration zone (70) is recycled to the second reaction zone (20). The anhydride can be directly recycled to the second reaction zone when the second solvent is the same as the aprotic organic solvent charged in the first reaction zone or when the thermal dehydration is conducted in the absence of a solvent. When the second solvent is present and different from the aprotic organic solvent charged to the first reaction zone, the anhydride stream (71) containing the second solvent is introduced to a third separation zone (110) to recover the second solvent (112), and the anhydride is directly recycled to the second reaction zone or the anhydride is contacted with a solvent (111), which is the same as the aprotic organic solvent charged to the first reaction zone, and recycled to the second reaction zone.

The separation in the third separation zone is accomplished by any conventional method known to those of ordinary skill in the art. Examples of such methods include, but are not limited to, distillation, thin film evaporation, crystallization, and the like. The temperature and pressure used in the third separation zone will depend on the particular method utilized and the solvent to be recovered.

According to either the first or second embodiments, the second product stream (32) can be introduced to a first fractionation zone (90) and fractionated to produce an aprotic organic solvent stream (91) and an isocyanate stream (92). The isocyanate stream can then be introduced to a second fractionation zone (100) and fractionated to produce a purified isocyanate product stream (101) and a by-product stream (102). The conditions of temperature and pressure in the first and second fractionation zones, and the configuration of the fractionation columns will be readily apparent to those of ordinary skill in the art depending on the aprotic organic solvent, isocyanate and by-products present in the isocyanate stream.

Once the aprotic organic solvent is recovered from the first fractionation zone, it can be recycled to the first reaction zone.

When a solvent exchange step is utilized in the separation of the first separation zone, i.e. when the aprotic organic solvent is water miscible, the second product stream will contain the water immiscible solvent instead of the water miscible aprotic organic solvent and it will be necessary to recover the water immiscible solvent from the second product stream in the first fractionation zone and a third fractionation zone may be required to purify the exchanged aprotic organic solvent prior to recycling the aprotic organic solvent to the first reaction zone.

According to the second embodiment, the recovered base salt of (c) is introduced to an electrodialysis zone (80) to produce a base stream (81) comprising the base and an organic acid stream (82) wherein the organic acid corresponds to the anhydride. The electrodialysis of the second embodiment to produce the organic acid is accomplished by any of the electrodialysis processes described above. Depending on the particular base salt, it may be necessary to contact the base salt with water prior to liberation of the base.

The base stream (81) is then introduced to the second separation zone (50), as described above, and the recovered base is recycled to the first reaction zone. The organic acid stream is introduced to the thermal dehydration zone, as described above, to produce the anhydride which is then recycled to the second reaction zone as described above.

Contemplated equivalence of the general formulas set forth above for the primary amines, isocyanates and anhydride dehydrating agents are compounds otherwise corresponding thereto and having the same general properties wherein one or more of the various R groups are simple variations of the substituents as defined therein.

In addition, where a substituent is designated as, or can be, a hydrogen, the exact chemical nature of a substituent which is other than hydrogen at that position is not critical so long as it does not adversely effect the overall synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

The invention will now be further disclosed in the following illustrative examples wherein parts and percentages are given on a molar basis unless otherwise specified.

EXAMPLES

Amines used in the following examples were obtained from Aldrich Chemical Company or Kodak Chemical Company, except as noted, and were used as received. Acetonitrile, toluene, methylene chloride and triethylamine were purchased from Aldrich Chemical Company. 2-Sulfobenzoic anhydride was obtained from Fluka Chemical Corp. CyTEG (N-cyclohexyl-N',N',N'',N''-tetraethyl guanidine) was synthesized according to the general procedure set forth in Bredereck, H. and Bredereck, K., Chem. Ber., 94, 2278–2295 (1961). Carbon dioxide was supplied either from Matheson (bone dry grade) or from Acetylene Gas Company (welding grade) and used without any further purification.

Gas chromatographic analysis was performed on a Varian model 3400 gas chromatograph with a model 8000 auto sampler using a 30 meter Megabore DB-1 (3 μm) J&W Scientific column.

Example 1 n-Octyl isocyanate: A Fischer-Porter bottle was charged with 1.29 g (10 mmol) n-octyl amine, 3 g (30 mmol) triethylamine, 154 mg (1 mmol) biphenyl as G.C. internal standard and 20 mL $CH_3CN$. At room temperature, 80 psig carbon dioxide was added above this solution (white ppt. formed upon $CO_2$ addition which went homogeneous within 5 min). After 1 h this solution was cooled to ca. 0° C. A second Fischer-Porter bottle was charged with 2.7 g (15 mmol) 2-sulfobenzoic anhydride (obtained from Fluka and used as received) and 20 mL $CH_3CN$ (homogeneous solution). After 1 h this solution was also cooled to 0° C. The carbamate solution generated in the first Fischer-Porter bottle was added all at once to the sulfobenzoic anhydride solution under 80 psig $CO_2$ giving an exothermic reaction (solution warmed from 0° C. to 11° C.). Aliquots were taken periodically and each diluted with diethyl ether and analyzed by G.C.. G.C. yield of n-octyl isocyanate after 5 min was calculated to be 94% (Run 1).

Additional runs (Runs 2–6) were made according to the above procedure varying the type and amount of base, solvent and the amount of 2-sulfobenzoic anhydride. The results of all runs can be found in Table I.

TABLE I

Reaction of n-Octyl Amine Carbamate with 2-Sulfobenzoic Anhydride[1]

| Run No. | Base, mmol CyTEG | Base, mmol Et$_3$N | Solvent | 2-Sulfobenzoic Anhydride (mmol) | % Yield n-Octyl-NCO |
|---|---|---|---|---|---|
| 1 | 0 | 30 | CH$_3$CN | 15 | 94 |
| 2 | 0 | 20 | CH$_3$CN | 15 | 82.5 |
| 3 | 0 | 40 | CH$_3$CN | 15 | 77.5 |
| 4 | 11 | 20 | CH$_2$Cl$_2$ | 10 | 62 |
| 5 | 11 | 20 | CH$_2$Cl$_2$ | 15 | 87.5 |
| 5 | 11 | 20 | toluene | 15 | 67 |

[1]All reactions were run with 10 mmol n-octyl amine under 80 psig $CO_2$ at ca. 0° C. All reactions were exothermic and yields of n-octyl isocyanate were determined by gas chromatographic analysis using biphenyl as an internal standard. Reaction time to maximum yield was 5–60 min in all runs except Run 6 (reaction in toluene as solvent) which was 3.5 hr.

Examples 2

Hexamethylene diisocyanate (HDI): The following is the general experimental procedure for runs 7–11. A three-neck, round-bottom flask was charged with 2.0 g (17 mmol) hexamethylenediamine from the Monsanto Company, 15 mL (109 mmol) triethylamine (TEA), 100 mL acetonitrile and 0.261 g (1.7 mmol) biphenyl as a G.C. internal standard. An overhead stirrer was placed in the center neck, a septum was placed in one side neck, and a dry ice condenser was placed in the other side neck. A thermocouple and a needle for $CO_2$ addition were inserted through the septum. A mixture of dry ice and m-xylene (mp = −47.9° C.) was placed in the dry ice condenses to keep solvents in the reaction flask. $CO_2$ addition was controlled with a rotameter and made subsurface through the addition needle. A mineral oil bubble was used to prevent back-flow of air into the reactor.

The reaction was initiated by adding $CO_2$ at room temperature to the solution with moderate stirring resulting in a $CO_2$ pressure of 0 psig, i.e. atmospheric $CO_2$ pressure. A heterogeneous solution resulted as the ammonium carbamate salt of hexamethylenediamine formed. A moderate exotherm was normally observed, i.e. a temperature increase of about 10° C. The temperature of the reaction mixture was then ramped to 0° C. over a 90 minute period using a water bath cooled by the addition of ice. After 90 minutes, the reaction mixture was cooled to −20° C. over a 30 minute period using an o-xylene/dry ice bath. After the reaction mixture reached −20° C., 68 mmol of 2-sulfobenzoic anhydride (SBA) was added as a solid in small increments over a 30 minute period.

After addition of the SBA was completed, the reaction mixture was sampled for analysis by Gas Chromatography. The sampling was done by adding 0.5 mL of the reaction mixture to a vial containing 2 mL of 0.5M HCl in $H_2O$ and 2 mL of toluene. The vial was shaken vigorously, allowed to settle and the toluene layer analyzed for HDI by Gas Chromatography using the biphenyl as an internal standard. The reaction mixture was removed from the dry ice bath and allowed to warm to room temperature. Sampling was continued over this time. Maximum yield normally was reached by 10 minutes after addition of the SBA was completed.

Run 7 was run at the above conditions. Run 8 was run at an increased level of TEA, i.e. 170 mmol TEA v. 109 mmol TEA. Run 9 utilized 100 mL chlorobenzene as solvent instead of 100 mL acetonitrile. Run 10 was run under the following different conditions: 34 mmol HDA, 218 mmol TEA, 138 mmol SBA dissolved in 80 mL acetonitrile and added as a solution, and $CO_2$ pressure of 30 psig. Run 11 was the same as run 10 except the $CO_2$ pressure was 0 psig. The yield results of runs 7–11 can be found in Table II.

TABLE II

| Run No. | % Yield HDI |
|---|---|
| 7 | 78 |
| 8 | 78 |
| 9 | 63 |
| 10 | 80 |
| 11 | 81 |

Example 3

This example demonstrates the hydrolysis of the linear anhydride salt of 2-sulfobenzoic anhydride and triethyl amine (I) to o-sulfobenzoic acid monotriethylammonium salt.

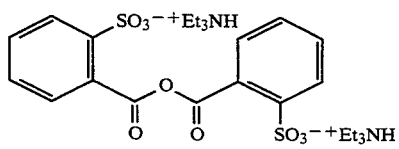

(I)

The linear anhydride salt, I, (0.5 g, 0.85 mmol) was dissolved in 13 mL water and heated to reflux with 1 mL aliquots taken after 45 and 90 minutes. These aliquots were dissolved in 15 mL acetonitrile and concentrated in vacuo. The resulting colorless oil was dissolved in 10 mL anhydrous acetonitrile and infrared analysis indicated the formation of o-sulfobenzoic acid monotriethylammonium salt. IR ($CH_3CN$) 1717 (S), 1823 (W).

Independent synthesis and insolation of the monotriethylammonium salt of o-sulfobenzoic acid was accomplished by addition of o-sulfobenzoic acid.$3H_2O$ (0.87 g, 3.4 mmol) to an aqueous (25 mL) solution of triethylamine (0.344 g, 0.34 mmol). Attempted extraction with either chloroform or diethylether gave only traces of material. Concentration of the aqueous solution in vacuo gave an oil which was dissolved in acetonitrile and dried over $MgSO_4$. IR ($CH_3CN$) 1719 (S), 1823 (w).

Example 4

This example demonstrates the conversion of the linear anhydride salt (I) to the disodium salt of sulfobenzoic acid and the recovery of triethylamine.

A 100 mL round bottom flask was sequentially charged with 5.88 g (10 mmol) of (I), 40 mL of distilled water and 1.66 g (40.2 mmol) NaOH pellets. The addition of the solid caustic caused an exothermic reaction and after stirring for 20 minutes the flask was attached to a distillation head and the triethylamine/water azeotrope collected (bp=78° C., pot temp.=95° C.). The distillate was diluted with an additional 50 mL of $H_2O$ and the quantity of triethylamine recovered was determined by titration with a standard solution of HCl (2 drops of bromothymol blue indicator; 0.1% solution in 50% ethanol/water). A 66% recovery of triethylamine was obtained via simple azeotropic distillation. The pure disodium salt of sulfobenzoic acid (4.7 g, 95% of theoretical) was recovered following removal with the aqueous solution in vacuo and drying overnight at 90° C. under dynamic vacuum.

Example 5

This example demonstrates the conversion of disodium 2-sulfobenzoate, i.e. the disodium salt of sulfobenzoic acid, to 2-sulfobenzoic acid.

Amberlite ® IR-120 (H+) ion exchange resin available from the Rohm & Haas Company was slurried with deionized water into a titration buret containing water and a glass wool plug at the bottom of the buret. After the buret was approximately one-half filled with resin, the system was backwashed with water until the resin remained fluidized for a few minutes. The resin was then allowed to settle and after settling occupied a volume of 27.5 mL. At 1.9 meg/mL, the total meg of resin in the bed was calculated to be 52.25. To insure that all acid sites of the resin were in the H+ form, the resin bed was washed with 28 mL 1N HCl and then rinsed with water until the pH returned to neutral.

2-Sulfobenzoic acid x $H_2O$ (Aldrich, x=3 by dehydration over $P_2O_5$ under vacuum), (3.59 g, 14.0 mmol) was dissolved in 140 mL water in a flask. 28 mL 1.00N NaOH was added to the 2-sulfobenzoic acid and the mixture stirred. The pH of the resulting disodium salt solution was 10.5.

The water level in the buret was within 2–3 cm above the resin level. The disodium salt solution was then pumped into the buret at 2.9 mL/minute (6.3 bed volumes per hour) while liquid was drained from the bottom of the buret at the same rate. The disodium salt solution was pumped using a Masterflex peristaltic type pump and the tubing used was an acid resistant type (Masterflex C-Flex 6424-14). The following observations of pH v. time (Table III) were recorded.

TABLE III

| Time, Min | Event |
|---|---|
| 0 | Start |
| 5 | pH of eluted solution = 6 |
| 15 | pH of eluted solution = 0 |
| 61 | pH = 0[1] |
| 68 | pH = 0 |
| 73 | pH = 3 |
| 80 | pH = 4.5 |
| 88 | pH = 6.0; Stop collecting |

[1] All of the disodium salt solution was out of the flask at this time. 10 mL water was used to rinse the flask and this was pumped through to the buret. This was followed by pumping pure deionized water to the buret.

The total eluted material was titrated with 1.00N NaOH using a phenolphthalein indicator. A total of 28.05 mL (28.05 mmol) NaOH was required to turn the indicator pink. This indicated that all of the disodium salt had been converted to the diacid and eluted from the resin bed.

The resin was then regenerated using 15 mL concentrated sulfuric acid (270 mmol) dissolved in 200 mL water. The sulfuric acid solution was pumped through the resin bed at 6 mL/minute followed by 5.7 bed volumes of deionized water at 5.6 mL/minute. The pH of the eluent after the deionized water was 7.0.

A second cycle of disodium salt of 2-sulfobenzoic acid was run through the resin bed in an identical manner as described above. As above, titration of the eluted material with 1.00N NaOH required 28.05 mL (28.05 mmol) NaOH indicating that complete conversion of the disodium salt to the diacid had occurred, i.e. a quantitative yield of diacid was calculated.

Example 6

This example demonstrates the conversion of calcium 2-sulfobenzoate to 2-sulfobenzoic acid, and the resulting conversion of the acid to 2-sulfobenzoic anhydride.

A 50 mL round bottom flask was charged with 5 mL water and 0.99 g (10.2 mmol) concentrated sulfuric acid. The addition of 2.45 g (10.2 mmol) calcium 2-sulfobenzoate as a solid to the stirred sulfuric acid solution caused an exothermic reaction and rapid dissolution of the solid. A white precipitate of $CaSO_4$ formed within 5 minutes and stirring was continued for an additional 20 minutes after which time the solids were removed by filtration. Removal of the water in vacuo gave 2.57 g (9.69 mmol, 95% yield) of pure 2-sulfobenzoic acid trihydrate as a white solid. The pure acid was charged into a 100 mL round bottom flask and diluted with 50 mL toluene. A Dean Stark was attached to the flask and the solution was refluxed for 3 hours. The toluene was removed in vacuo and the resulting solid was analyzed using $^1H$ NMR and infrared spectroscopy revealing a 93% conversion of the diacid to 2-sulfobenzoic anhydride.

Example 7

The example demonstrates the preparation of 2-sulfobenzoic anhydride from 2-sulfobenzoic acid using two different solvents.

Method A: Into a 3-neck 100 mL round bottom flask fitted with a thermocouple well, a sampling system and a Dean-Stark trap with reflux condenser were charged 3.999 g (19.78 mmol) 2-sulfobenzoic acid (anhydrous, m.p.=139.5°–141° C.) and 20 mL cumene. The Dean-Stark trap was filled to the spillover point with cumene. The mixture was heated to reflux for 3.5 hours while the pot temperature ranged from 151°–153° C. Samples were taken intermittently and analyzed by titration for residual free acid and for total acidity after 25 minutes hydrolysis. The titration was a non-aqueous titration using tri-n-propylamine. The analyses indicated the following yields of 2-sulfobenzoic anhydride (Table IV).

TABLE IV

| Time, Hr | Yield, % |
|---|---|
| 0.75 | 90.6 |
| 1.5 | 95.9 |
| 2.5 | 97.3 |

TABLE IV-continued

| Time, Hr | Yield, % |
|---|---|
| 3.5 | 98.7 |

Method B: Into a 3-neck 100 mL round bottom flask fitted with a thermocouple well, a sampling system and a Dean-Stark trap with reflux condenser were charged 3.911 g (19.34 mmol) 2-sulfobenzoic acid, 1.667 g hexadecane (internal Gas Chromatography standard) and 20 mL mixed xylenes. The Dean-Stark trap was filled to the spillover point with xylenes. The mixture was heated to reflux for 4.5 hours while the pot temperature ranged from 139°141° C. Samples were taken intermittently and analyzed by gas chromatography vs. the hexadecane internal standard. The analyses indicated the following yields of 2-sulfobenzoic anhydride (Table V).

TABLE V

| Time, Hr | Yield, % |
|---|---|
| 1.0 | 81.6 |
| 2.0 | 91.9 |
| 3.0 | 97.0 |
| 4.5 | 97.1 |

That which is claimed is:

1. A process for preparing an isocyanate comprising:
   a) contacting $CO_2$ and a primary amine in the presence of an aprotic organic solvent and a base selected from the group consisting of a phosphazene compound, an organic nitrogenous base and mixtures thereof, wherein said organic, nitrogenous base is selected from the group consisting of guanidine compounds, amidine compounds, tertiary amines and mixtures thereof, in a first reaction zone under reaction conditions of time and temperature sufficient to produce the corresponding ammonium carbamate salt,
   b) passing the effluent stream of said first reaction zone into a second reaction zone and reacting said carbamate salt with an anhydride represented by the formula:

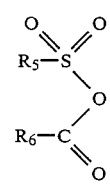

wherein $R_5$ and $R_6$ together form a cyclic anhydride or a cyclic anhydride containing a fused aromatic or fused cycloaliphatic ring, under reaction conditions of time and temperature sufficient to produce a first product stream containing the corresponding isocyanate, said aprotic organic solvent and the base salt derived from said anhydride,
   c) passing said first product stream to a first separation zone and separating said base salt derived from said anhydride from said first product stream to form a second product stream comprising said isocyanate and said aprotic organic solvent,
   d) contacting in a third reaction zone said recovered base salt of (c) with an inorganic compound selected from the group consisting of alkali metal hydroxides, alkaline earth metal hydroxides, alkaline earth metal oxides, alkali metal carbonates and alkaline earth metal carbonates in an amount effective to liberate the base from said base salt and form a first effluent stream containing the base and corresponding alkali metal or alkaline earth metal salt, e) introducing said first effluent stream into a second separation zone, separating the base from said first effluent stream and recycling the base to said first reaction zone, f) introducing the thus recovered alkali metal or alkaline earth metal salt into an organic acid production zone to convert said alkali metal or alkaline earth metal salt into the organic acid corresponding to said anhydride, g) optionally contacting said organic acid with a second solvent, h) thermally dehydrating said organic acid in a thermal dehydration zone under conditions of temperature and pressure to remove water and regenerate said anhydride, and i) recycling said anhydride to said second reaction zone, or when said second solvent is present and is different from said aprotic organic solvent, i') (1) introducing said anhydride and said second solvent into a third separation zone to recover said second solvent, and (2) (i) recycling said anhydride to said second reaction zone or (ii) contacting said anhydride with said aprotic organic solvent and recycling said anhydride to said second reaction zone.

2. The process of claim 1 wherein said organic acid of (f) is produced by contacting said recovered alkali metal or alkaline earth metal salt with an ion exchange resin.

3. The process of claim 2 wherein said ion exchange resin is periodically contacted with a mineral acid to regenerate said ion exchange resin and produce an alkali metal or alkaline earth metal salt of said mineral acid.

4. The process of claim 3 wherein said alkali metal or alkaline earth metal salt of said mineral acid is introduced into an electrodialysis zone and the resulting mineral acid and alkali metal or alkaline earth metal hydroxide product streams are recycled.

5. The process of claim 3 wherein said mineral acid is $H_2SO_4$ or HCl.

6. The process of claim 1 wherein said organic acid of (f) is produced by introducing said alkali metal or alkaline earth metal salt into an electrodialysis zone to produce an alkali metal or alkaline earth metal hydroxide and said organic acid.

7. The process of claim 6 wherein said alkali metal or alkaline earth metal hydroxide is recycled to said third reaction zone.

8. The process of claim 1 wherein said organic acid of (f) is produced by contacting said alkali metal or alkaline earth metal salt with a strong mineral or organic acid to produce said organic acid of (f) and an alkali metal or alkaline earth metal salt of said strong mineral or organic acid.

9. The process of claim 8 wherein when said organic acid of (f) is contacted with said second solvent prior to said thermal dehydration, said alkali metal or alkaline earth metal salt of said strong mineral or organic acid is (1) separated from said organic acid prior to said thermal dehydration or (2) separated from said anhydride prior to recycling said anhydride.

10. The process of claim 8 wherein when said thermal dehydration is conducted in the absence of said second solvent, the effluent stream of said thermal dehydration zone is contacted with a second solvent and said alkali metal or alkaline earth metal salt of said strong mineral or organic acid is separated from said anhydride prior to recycling said anhydride.

11. The process of claim 8 wherein the strong acid is a strong mineral acid.

12. The process of claim 11 wherein said strong mineral acid is $H_2SO_4$ or HCl.

13. The process of claim 1 wherein said second solvent is present and is immiscible with water and the thermal dehydration of (h) is conducted by heating the contents of said thermal dehydration zone to remove a mixture of water and said second solvent overhead, condensing said mixture of water and second solvent, phase separating said mixture of water and second solvent and refluxing said second solvent to said thermal dehydration zone.

14. The process of claim 1 wherein said thermal dehydration of (h) is conducted by heating the contents of said thermal dehydration zone in the presence of a desiccant.

15. The process of claim 14 wherein said desiccant is a molecular sieve.

16. The process of claim 1 wherein said separation in said first separation zone of said base salt from said first product stream is conducted by: (1) filtering said base salt from said first product stream to recover said base salt and a filtrate comprising said aprotic organic solvent, said isocyanate and a trace amount of said base salt, and (2) (i) when said aprotic organic solvent is water immiscible, extracting said trace amount of base salt from said filtrate with water to produce said second product stream, or (ii) when said aprotic organic solvent is water miscible, performing a solvent exchange on said filtrate to replace said water miscible aprotic organic solvent with a water immiscible solvent and extracting with water or filtering said trace amount of base salt from said filtrate to produce said second product stream wherein said recovered base salt of (2) is combined with said recovered base salt of (1).

17. The process of claim 1 further comprising:

j) introducing said second product stream to a first fractionation zone and fractionating said second product stream to produce an aprotic organic solvent stream and an isocyanate stream.

18. The process of claim 17 wherein said isocyanate stream is introduced to a second fractionation zone and fractionated to produce a purified isocyanate product stream and a by-product stream.

19. The process of claim 17 wherein said aprotic organic solvent stream is recycled to said first reaction zone.

20. The process of claim 1 wherein said separation of (e) is a steam distillation.

21. The process of claim 1 wherein said anhydride is 2-sulfobenzoic anhydride.

22. The process of claim 21 wherein said aprotic organic solvent is acetonitrile, propionitrile, chlorobenzene or dichlorobenzene and said base is triethylamine, dimethylcyclohexyl amine or methyldicyclohexylamine.

23. The process of claim 22 wherein said inorganic compound is sodium hydroxide or calcium hydroxide.

24. The process of claim 22 wherein a second solvent is present in (g) and said second solvent is xylene, cumene, toluene or chlorobenzene.

25. The process of claim 1 wherein said aprotic organic solvent is selected from the group consisting of acetonitrile, propionitrile, chlorobenzene, and dichlorobenzene.

26. The process of claim 1 wherein the ratio of the number of moles of said anhydride charged to said second reaction zone to the number of equivalents of amine in said primary amine starting material is about 0.4:1 to about 10:1.

27. The process of claim 1 wherein said primary amine is selected from the group consisting of compounds represented by the formula R—NH$_2$, polyoxyalkylene diamines represented by the formula:

$$H_2N \hspace{-2pt}-\hspace{-4pt}(\hspace{-2pt}CH\hspace{-2pt}-\hspace{-2pt}CH_2\hspace{-2pt}-\hspace{-2pt}O\hspace{-2pt})_{\overline{x}}\hspace{-2pt}(\hspace{-2pt}CH_2\hspace{-2pt}-\hspace{-2pt}CH_2\hspace{-2pt}-\hspace{-2pt}O\hspace{-2pt})_{\overline{z}}\hspace{-2pt}(\hspace{-2pt}CH\hspace{-2pt}-\hspace{-2pt}CH_2\hspace{-2pt}-\hspace{-2pt}O\hspace{-2pt})_{\overline{y}}CH_2\hspace{-2pt}-\hspace{-2pt}CH\hspace{-2pt}-\hspace{-2pt}NH_2$$
$$\hspace{40pt}|\hspace{110pt}|\hspace{90pt}|$$
$$\hspace{40pt}CH_3\hspace{100pt}CH_3\hspace{80pt}CH_3$$

and polyoxyalkylene triamines represented by the formula:

$$A \begin{cases} (OCH_2CH)_{\overline{a}}NH_2 \\ \hspace{10pt}|\\ \hspace{10pt}R_3 \\ (OCH_2CH)_bNH_2 \\ \hspace{10pt}|\\ \hspace{10pt}R_3 \\ (OCH_2CH)_{\overline{c}}NH_2 \\ \hspace{10pt}|\\ \hspace{10pt}R_3 \end{cases}$$

wherein R is selected from the group consisting of alkyl, alkenyl, cycloalkyl, cycloalkenyl, aryl, aralkyl, aralkenyl, alkenaryl and alkaryl radicals having 1 to about 22 carbon atoms, a radical represented by the formula:

$$+R_4)_{\overline{n}}(R_1)_{\overline{m}}NH_2$$
$$\hspace{30pt}|$$
$$\hspace{30pt}NH_2$$

and a radical represented by the formula —R$_4$—NH$_2$, or R as defined above containing nonnucleophilic functional groups; wherein R$_1$ and R$_4$ are independently selected from the group consisting of alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, R$_3$ is hydrogen or methyl, x+w represents an integer from about 2 to about 70, z represents an integer from 0 to about 90, x+w+z represents an integer from about 2 to about 100, a, b and c independently represent an integer from about 2 to about 30, and A represents a trihydric alcohol initiator.

28. The process of claim 1 wherein said isocyanate is represented by the formula:

$$R_2—N=C=$$

wherein R$_2$ is selected from the group consisting of alkyl, alkenyl, cycloalkyl, cycloalkenyl, aryl, aralkyl, aralkenyl, alkenaryl and alkaryl radicals having 1 to about 22 carbon atoms, a radical represented by the formula:

$$+R_4)_{\overline{n}}(R_1)_{\overline{m}}N=C=O$$
$$\hspace{30pt}|$$
$$\hspace{30pt}N=C=O$$

a radical represented by the formula:

$$—R_4—N=C=O,$$

a radical represented by the formula:

$$+CH—CH_2—O)_{\overline{x}}(CH_2—CH_2—O)_{\overline{z}}(CH—CH_2—O)_{\overline{w}}CH_2—CH—N=C=O$$
$$\hspace{10pt}|\hspace{110pt}|\hspace{90pt}|$$
$$\hspace{10pt}CH_3\hspace{100pt}CH_3\hspace{80pt}CH_3$$

or R$_2$ as defined above containing nonnucleophilic functional groups; or said isocyanate is represented by the formula:

$$A \begin{cases} (OCH_2CH)_{\overline{a}}N=C=O \\ \hspace{10pt}|\\ \hspace{10pt}R_3 \\ (OCH_2CH)_{\overline{b}}N=C=O \\ \hspace{10pt}|\\ \hspace{10pt}R_3 \\ (OCH_2CH)_{\overline{c}}N=C=O \\ \hspace{10pt}|\\ \hspace{10pt}R_3 \end{cases}$$

wherein R$_1$ and R$_4$ are independently selected from the group consisting of alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, R$_3$ is hydrogen or methyl, x+w represents an integer from about 2 to about 70, z represents an integer from 0 to about 90, x+w+z represents an integer from about 2 to about 100, a, b and c independently represent an integer from about 2 to about 30, and A represents a trihydric alcohol initiator.

29. The process of claim 1 wherein an ion exchange resin is contacted with said organic acid in said thermal dehydration zone.

30. The process of claim 29 wherein said organic acid is further contacted with a second solvent.

31. A process for preparing an isocyanate comprising:
a) contacting CO$_2$ and a primary amine in the presence of an aprotic organic solvent and a base selected from the group consisting of a phosphazene compound, an organic nitrogenous base and mixtures thereof, wherein said organic, nitrogenous base is selected from the group consisting of guanidine compounds, amidine compounds, tertiary amines and mixtures thereof, in a first reaction zone under reaction conditions of time and temperature sufficient to produce the corresponding ammonium carbamate salt,
b) passing the effluent stream of said first reaction zone into a second reaction zone and reacting said carbamate salt with an anhydride represented by the formula:

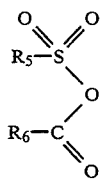

wherein $R_5$ and $R_6$ together form a cyclic anhydride or a cyclic anhydride containing a fused aromatic or fused cycloaliphatic ring, under reaction conditions of time and temperature sufficient to produce a first product stream containing the corresponding isocyanate, said aprotic organic solvent and the base salt derived from said anhydride, c) passing said first product stream to a first separation zone and separating said base salt derived from said anhydride from said first product stream to form a second product stream containing said isocyanate and said aprotic organic solvent, d) introducing said recovered base salt of (c) into an electrodialysis zone to produce a base stream comprising said base and an organic acid stream wherein said organic acid corresponds to said anhydride, e) introducing said base stream into a second separation zone, separating said base from said impurities to form a purified base stream, and recycling said base to said first reaction zone, f) optionally contacting said organic acid with a second solvent, g) thermally dehydrating said organic acid in a thermal dehydration zone under conditions of temperature and pressure to remove water and regenerate said anhydride, and h) recycling said anhydride to said second reaction zone, or when said second solvent is present and is different from said aprotic organic solvent, h') (1) introducing said anhydride and said second solvent into a third separation zone to recover said second solvent, and (2) (i) recycling said anhydride to said second reaction zone or (ii) contacting said anhydride with said aprotic organic solvent and recycling said anhydride to said second reaction zone.

32. The process of claim 31 wherein said second solvent is present and is immiscible with water and the thermal dehydration of (g) is conducted by heating the contents of said thermal dehydration zone to remove a mixture of water and said second solvent overhead, condensing said mixture of water and second solvent, phase separating said mixture of water and second solvent and refluxing said second solvent to said thermal dehydration zone.

33. The process of claim 31 wherein said thermal dehydration of (g) is conducted by heating the contents of said thermal dehydration zone in the presence of a desiccant.

34. The process of claim 33 wherein said desiccant is a molecular sieve.

35. The process of claim 31 wherein said separation in said first separation zone of said base salt from said first product stream is conducted by: (1) filtering said base salt from said first product stream to recover said base salt and a filtrate comprising said aprotic organic solvent, said isocyanate and a trace amount of said base salt, and (2) (i) when said aprotic organic solvent is water immiscible, extracting said trace amount of base salt from said filtrate with water to produce said second product stream, or (ii) when said aprotic solvent is water miscible, performing a solvent exchange on said filtrate to replace said water miscible aprotic organic solvent with a water immiscible solvent and extracting with water or filtering said trace amount of base salt from said filtrate to produce said second product stream wherein said recovered base salt of (2) is combined with said recovered base salt of (1).

36. The process of claim 31 further comprising:
    i) introducing said second product stream to a first fractionation zone and fractionating said second product stream to produce an aprotic organic solvent stream and an isocyanate stream.

37. The process of claim 36 wherein said isocyanate stream is introduced to a second fractionation zone and fractionated to produce a purified isocyanate product stream and a by-product stream.

38. The process of claim 36 wherein said aprotic organic solvent stream is recycled to said first reaction zone.

39. The process of claim 31 wherein said separation of (e) is a steam distillation.

40. The process of claim 31 wherein said anhydride is 2-sulfobenzoic anhydride.

41. The process of claim 40 wherein said aprotic organic solvent is acetonitrile, propionitrile, chlorobenzene or dichlorobenzene and said base is triethylamine, dimethylcyclohexylamine or methyldicylohexylamine.

42. The process of claim 41 wherein said inorganic compound is sodium hydroxide or calcium hydroxide.

43. The process of claim 41 wherein a second solvent is present in (g) and said second solvent is xylene, cumene, toluene or chlorobenzene.

44. The process of claim 31 wherein said aprotic organic solvent is selected from the group consisting of dichloromethane, tetrahydrofuran, acetonitrile, o-dichlorobenzene, toluene, N,N-dimethylacetamide and pyridine.

45. The process of claim 31 wherein the ratio of the number of moles of said anhydride charged in to said second reaction zone to the number of equivalents of amine in said primary amine starting material is about 0.4:1 to about 10:1.

46. The process of claim 31 wherein said primary amine is selected from the group consisting of compounds represented by the formula R—NH$_2$, polyoxyalkylene diamines represented by the formula:

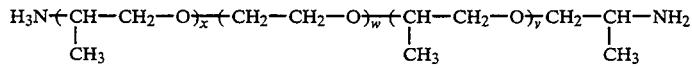

and polyoxyalkylene triamines represented by the formula:

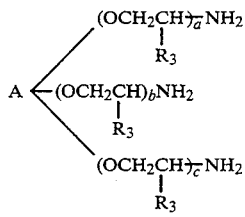

wherein R is selected from the group consisting of alkyl, alkenyl, cycloalkyl, cycloalkenyl, aryl, aralkyl, aralkenyl, alkenaryl and alkaryl radicals having 1 to about 22 carbon atoms, a radical represented by the formula:

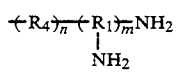

and a radical represented by the formula —$R_4$—$NH_2$, or R as defined above containing nonnucleophilic functional groups; wherein $R_1$ and $R_4$ are independently selected from the group consisting of alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, $R_3$ is hydrogen or methyl, x+w represents an integer from about 2 to about 70, z represents an integer from 0 to about 90, x+w+z represents an integer from about 2 to about 100, a, b and c independently represent an integer from about 2 to about 30, and A represents a trihydric alcohol initiator.

47. The process of claim 31 wherein said isocyanate is represented by the formula:

$$R_2—N=C=O$$

wherein $R_2$ is selected from the group consisting of alkyl, alkenyl, cycloalkyl, cycloalkenyl, aryl, aralkyl, aralkenyl, alkenaryl and alkaryl radicals having 1 to about 22 carbon atoms, a radical represented by the formula:

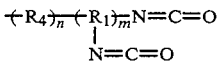

a radical represented by the formula:

—$R_4$—N=C=C, a radical represented by the formula:

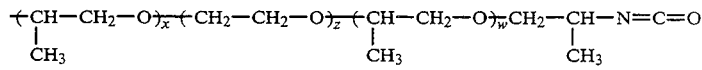

or $R_2$ as defined above containing nonnucleophilic functional groups; or said isocyanate is represented by the formula:

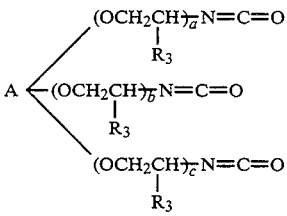

wherein $R_1$ and $R_4$ are independently selected from the group consisting of alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, $R_3$ is hydrogen or methyl, x+w represents an integer from about 2 to about 70, z represents an integer from 0 to about 90, x+w+z represents an integer from about 2 to about 100, a, b and c independently represent an integer from about 2 to about 30, and A represents a trihydric alcohol initiator.

48. The process of claim 31 wherein an ion exchange resin is contacted with said organic acid in said thermal dehydration zone.

49. The process of claim 48 wherein said organic acid is further contacted with a second solvent.

* * * * *